(12) United States Patent
Cravatt

(10) Patent No.: US 7,351,874 B2
(45) Date of Patent: Apr. 1, 2008

(54) MOUSE MODEL FOR FATTY ACID AMIDE-RELATED NEUROBEHAVIORS

(75) Inventor: Benjamin F. Cravatt, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 466 days.

(21) Appl. No.: 10/209,002

(22) Filed: Jul. 30, 2002

(65) Prior Publication Data

US 2003/0041340 A1    Feb. 27, 2003

Related U.S. Application Data

(60) Provisional application No. 60/309,098, filed on Jul. 31, 2001.

(51) Int. Cl.
  G01N 33/00    (2006.01)
  A01K 67/027    (2006.01)
(52) U.S. Cl. ............................................ 800/3; 800/18
(58) Field of Classification Search .................... 800/3, 800/13–20, 25; 435/320.1, 325, 354; 514/1
  See application file for complete search history.

(56) References Cited

OTHER PUBLICATIONS

Bisogno et al. Arachidonoylserotonin and Other Novel Inhibitors of Fatty Acid Amide Hydrolase. Biochem. Biophys. Res. Comm. 1998, vol. 248, No. 3, pp. 515-522.*
Capecchi , M. The New Mouse Genetics: Altering the Mouse Genome by Gene Targeting. Trends in Genetics. 1989, vol. 5, pp. 70-76.*
Moreadith, R. W. Gene Targeting in Embryonic Stem Cells: the New Physiology and Metabolism. J. Molecular Med. 1997, vol. 75, pp. 208-216.*
Wheeler, M. B. et al. Transgenic Technology and Applications in Swine. Theriogenelogy. 2001, vol. 56, pp. 1345-1369.*
Prelle, K. et al. Establishment of Pluripotent Cell Lines from Vertebrate Species—Present Status and Future Prospects. Cells Tissues Organs. 1999, vol. 165, pp. 220-236.*
va de Lavoir et al. High-Grade Transgenic Somatic Chimeras from Chicken Embryonic Stem Cells. Mechanisms of Development. 2006, vol. 123, pp. 31-41.*
Sang, H. Prospects for Transgenesis in the Chick. Mechanisms of Development. 2004, vol. 121, pp. 1179-1186.*
Petitte et al. Avian Pluripotent Stem Cells. Mechanisms of Development. 2004, vol. 121, pp. 1159-1168.*
Fan et al. Development of Cell Cultures with Competency for Contributing to the Zebrafish Germ Line. Critical Reviews in Eurkaryotic Gene Expression. 2004, vol. 14, pp. 43-51.*
Marzo et al., "Levels, Metabolism, and Pharmacological Activity of Anandamide in $CB_1$ Cannabinoid Receptor Knockout Mice: Evidence for Non-$CB_1$ , Non-$CB_2$ Receptor-Mediated Actions of Anandamide in Mouse Brain," *Journal of Neurochemistry*, vol. 75, No. 6, pp. 2434-2444 (2000).
Patricelli et al., "Chemical and Mutagenic Investigations of Fatty Acid Amide Hydrolase: Evidence for a Family Serine Hydrolases with Distinct Catalytic Properties," *Biochemistry*, vol. 98, pp. 9804-9812 (1999).
Patricelli et al., "Comparative Characterization of a Wild Type and Transmembrane Domain-Deleted Fatty Acid Amide Hydrolase: Identification of the Transmembrane Domain as a Site for Oligomerization," *Biochemistry*, vol. 37, pp. 15177-15187 (1998).
Cao, et al., "Primary afferent tachykinins are required to experience moderate to intense pain," *Nature*, vol. 392, pp. 390-394, Mar. 26, 1998.
Giang and Cravatt, "Molecular characterization of human and mouse fatty acid amide hydrolases," *Proc. Natl. Acad. Sci. USA*, vol. 94, pp. 2238-2243, Mar. 1997.
Cravatt et al., "Molecular characterization of an enzyme that degrades neuromodulatroy fatty-acid amides," *Nature*, vol. 384, pp. 83-87, Nov. 7, 1996.
Mechoulam et al., Anandamide May Mediate Sleep Induction, *Nature*, Sep. 4, 1997, vol. 389, pp. 25-26.
Wan et al., Conserved Chromosomal Location and Genomic Structure of Human and Mouse Fatty-Acid Amide Hydrolase Genes and Evaluation of Clasper as a Candidate *Neurological Mutation Genomics*, 1998, vol. 54, pp. 408-414.
Aoyama et al., Altered Constituitive Expression of Fatty Acid-Metabolizing Enzymes in Mice Lacking the Peroxisome Proliferator-Activated Receptor Alpha (PPAR-alpha), *Journal of Biological Chemistry*, Mar. 6, 1998, vol. 273, No. 10, pp. 5678-5684.
Thomas et al., "Fatty Acid Amide Hydrolase, the Degradative Enzyme for Anandamide and Oleamide, Has Selective Distribution in Neurons Within the Rat Central Nervous System", *Journal of Neuroscience Research* 1997, vol. 50, 1047-1052.
Bisogno et al., The Sleep Inducing Factor Oleamide is Produced by Mouse Neuroblastoma Cells, *Biochemical and Biophysical Research Communications*, 1997, vol. 239, pp. 473-479.
Cravatt, et al., "Supersensitivity to Anandamide and Enhanced Endogenous Cannabinoid Signaling in Mice Lacking Fatty Acid Amide Hydrolase", *PNAS 98*, 16: 9371-9376 (2001).

* cited by examiner

*Primary Examiner*—Deborah Crouch
(74) *Attorney, Agent, or Firm*—Hugh Wang; Thomas Fitting; Michael J. McCarthy

(57) ABSTRACT

The invention relates to an animal model for studying behavior related to fatty acid amide and hydrolysis of fatty acid amide. The invention provides transgenic animals in which the protein fatty acid amide hydrolase is not expressed, and methods of using such animals.

7 Claims, 6 Drawing Sheets

MOUSE MODEL FOR FATTY ACID AMIDE-RELATED NEUROBEHAVIORS

This application claims priority under 35 U.S.C. §119(e) to U.S. Provisional Application Ser. No. 60/309,098 filed Jul. 31, 2001, the contents of which are incorporated herein by reference in its entirety.

ACKNOWLEDGEMENT OF GOVERNMENT SUPPORT

This invention was made in part with government support under Grant No. MH-58542 awarded by the National Institute of Mental Health of the National Institutes of Health. The government may have certain rights in this invention.

FIELD OF THE INVENTION

The invention relates generally to animal model systems useful for examining and manipulating the half-life of bioactive molecules that influence behavior, and, more specifically, to fatty acid amide hydrolase (FAAH) gene knockout mice and to methods of using the knockout mice to identify agents that alleviates pain or modulate other behaviors.

BACKGROUND INFORMATION

The in vivo levels of chemical messengers like the fatty acid amides are tightly regulated to maintain proper control over their influence on brain and body physiology. One mechanism by which the level of fatty acid amides are regulated in vivo is through an enzyme termed fatty acid amide hydrolase (FAAH) which degrades the fatty acid amides to inactive metabolites. FAAH effectively terminates the signaling messages conveyed by fatty acid amides, ensuring that these molecules do not generate physiological responses in excess of their intended purpose. In the presence of FAAH, therefore, it is difficult, if not impossible to assess the pharmacological and physiological activities of fatty acid amides and related compounds.

Thus, a need exists for a transgenic animal in which FAAH is not expressed. The present invention satisfies this need and provides additional advantages.

SUMMARY OF THE INVENTION

The present invention relates to transgenic non-human animals having a disruption in the gene expressing fatty acid amide hydrolase (FAAH). One role of FAAH is the enzymatic degradation of a natural brain lipid, N-arachidonoyl-ethanolamine ("anandamide"), a neuroactive molecule that has been characterized as a endogenous ligand for the $CB_1$ receptor. Anandamide mediates a variety of behaviors including pain perception, cognition, feeding, epilepsy, motility and thermoregulation. Transgenic animals having a disruption in the FAAH gene are models for determining FAAH-specific compounds and for confirming and assessing activities mediated by fatty acid amides and related compounds.

The present invention provides a transgenic non-human animal having a transgene disrupting or interfering with expression of fatty acid amide hydrolase chromosomally integrated into germ cells of the animal.

Also provided by the present invention is a transgenic mouse comprising a disruption in the fatty acid amide hydrolase gene. The disruption of the FAAH gene results in an inability of the mouse to produce detectable levels of FAAH.

The invention also provides a method for producing a transgenic mouse exhibiting an inability to produce detectable levels of FAAH. The method includes introducing a transgene into a mouse embryonic stem cell, introducing the stem cell into a mouse embryo, transplanting the embryo into a pseudopregnant mouse and allowing the embryo to develop to term.

The invention further provides a method for identifying a compound that specifically inhibits FAAH activity. The method includes comparing the level of a fatty acid amide following administration of the compound to a non-transgenic mouse to the level of the fatty acid amide in a FAAH transgenic mouse. A similar level of fatty acid amide in the transgenic and non-transgenic mice indicates a compound that specifically inhibits FAAH production or activity.

A method is also provided for screening a candidate agent for the ability to modulate behavior in a FAAH transgenic animal. The method includes administering to a first transgenic animal a candidate agent and comparing the behavior of the animal to the behaviors of a second transgenic animal not administered the candidate agent and a non-transgenic animal administered the candidate agent.

A method is also provided to screen for a compound that acts as a substrate for FAAH in vivo. The method includes administering the compound to non-transgenic and FAAH transgenic animals and comparing the levels of the compound and its metabolites in these animals. A greater level of the compound in FAAH transgenic animals indicates a compound that is a substrate for FAAH in vivo.

BRIEF DESCRIPTION OF THE DRAWINGS

FIG. 1 shows the genomic structure surrounding the deleted FAAH exon 1 (E1). Only relevant restriction sites are designated. The deleted E1 exon encodes amino acids 1-65 of the FAAH protein.

FIG. 2A shows the results of the hypomotility (locomotor activity) study. ED50<6.25 mg/kg. FIG. 2B shows the results of the antinociception (tail-immersion) study; ED50 (95% confidence limit; "C.L.")=13 (5 to 30 mg/kg). % MPE indicates percent of maximum possible effect (see Example 3). FIG. 2C shows the results of the catalepsy study; ED50 (C.L.)=20 (11 to 35 mg/kg). FIG. 2D shows the results of the hypothermia (rectal temperature) study; ED50 (C.L.)=11 (6 to 19 mg/kg). ι-p<0.05, ιι-p<0.01 or ιιι-p<0.001, for FAAH$^{-/-}$ versus FAAH$^{+/+}$ mice receiving the same treatment (planned comparison). *-p<0.05 or -p<0.01 for anandamide-treated versus vehicle-treated FAAH$^{-/-}$ mice (Dunnett's test). FIGS. 2E and 2F show the time course of the hypothermia (FIG. 2E) and catalepsy (FIG. 2F) in mice treated with either vehicle (FAAH$^{+/+}$, open circles; FAAH$^{-/-}$, filled circles) or 50 mg/kg anandamide (FAAH$^{+/+}$, open squares; FAAH$^{-/-}$, filled squares). *-p<0.001 for anandamide-treated FAAH$^{-/-}$ mice versus the other three test groups (Scheffe test). Results are shown as mean ±S.E; n=6 to 8 mice/group.

SR141716A (10 mg/kg) completely blocked the hypomotility (FIG. 3A), antinociception (FIG. 3B), catalepsy (FIG. 3C), and hypothermia (FIG. 3D) induced by anandamide (50 mg/kg); SR141716A-pretreated, anandamide-treated FAAH$^{-/-}$ mice were indistinguishable in all behavioral assays from FAAH$^{-/-}$ mice treated with vehicle alone (0 mg/kg anandamide; see FIGS. 2A to 2D). -p<0.01; *-p<0.001 for SR141716A-treated versus vehicle-treated FAAH$^{-/-}$ mice (planned comparison). The results are presented as mean ⊥S.E; n=6-8 mice/group.

Figure 4:
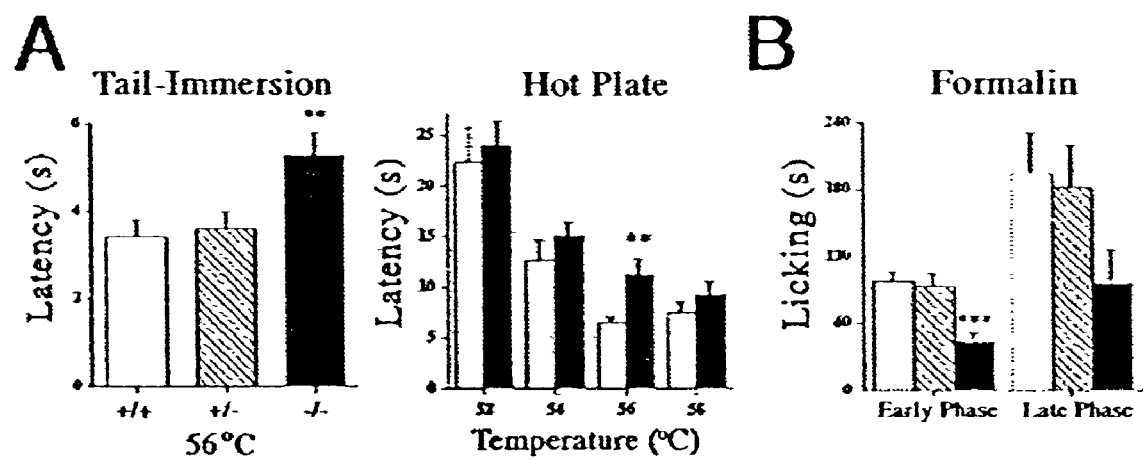

FIG. 4 shows that FAAH-/- mice display altered thermal pain sensation. FIG. 4A shows that FAAH-/- mice exhibit prolonged response latencies when compared to both FAAH+/+ and +/- mice in the tail immersion test and the hot plate test for chemical pain sensation. FIG. 4B shows that FAAH-/- mice exhibit a significant reduction in pain behavior during the first phase of the formalin test relative to both FAAH+/+ and +/- mice.

Figure 5:
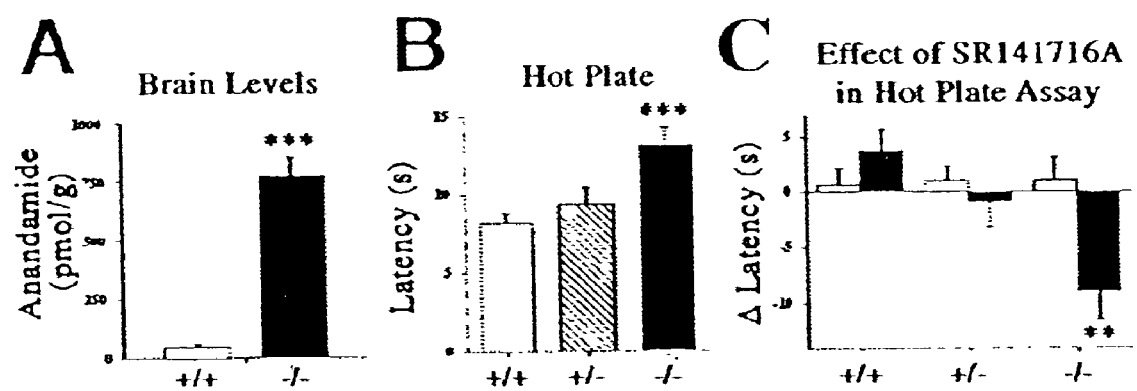

FIG. 5 shows the endogenous cannabinoid levels and activity of FAAH mice. FIG. 5A shows that brains from FAAH-/- mice possess 15-fold higher levels of anandamide than brains from FAAH+/+ mice. FIGS. 5B and 5C show the results of FAAH-/-, FAAH+/+, and FAAH+/- mice tested in the hot plate test both prior to and after treatment with either vehicle or SR141716A. No significant change from baseline were observed for the hot plate response latencies of vehicle-treated FAAH+/+, +/-, and -/- mice, or in SR141617A-treated FAAH+/+ and +/- mice. In contrast, FAAH-/- mice treated with SR141716A show a dramatic reduction in their pain response latencies.

Figure 6:
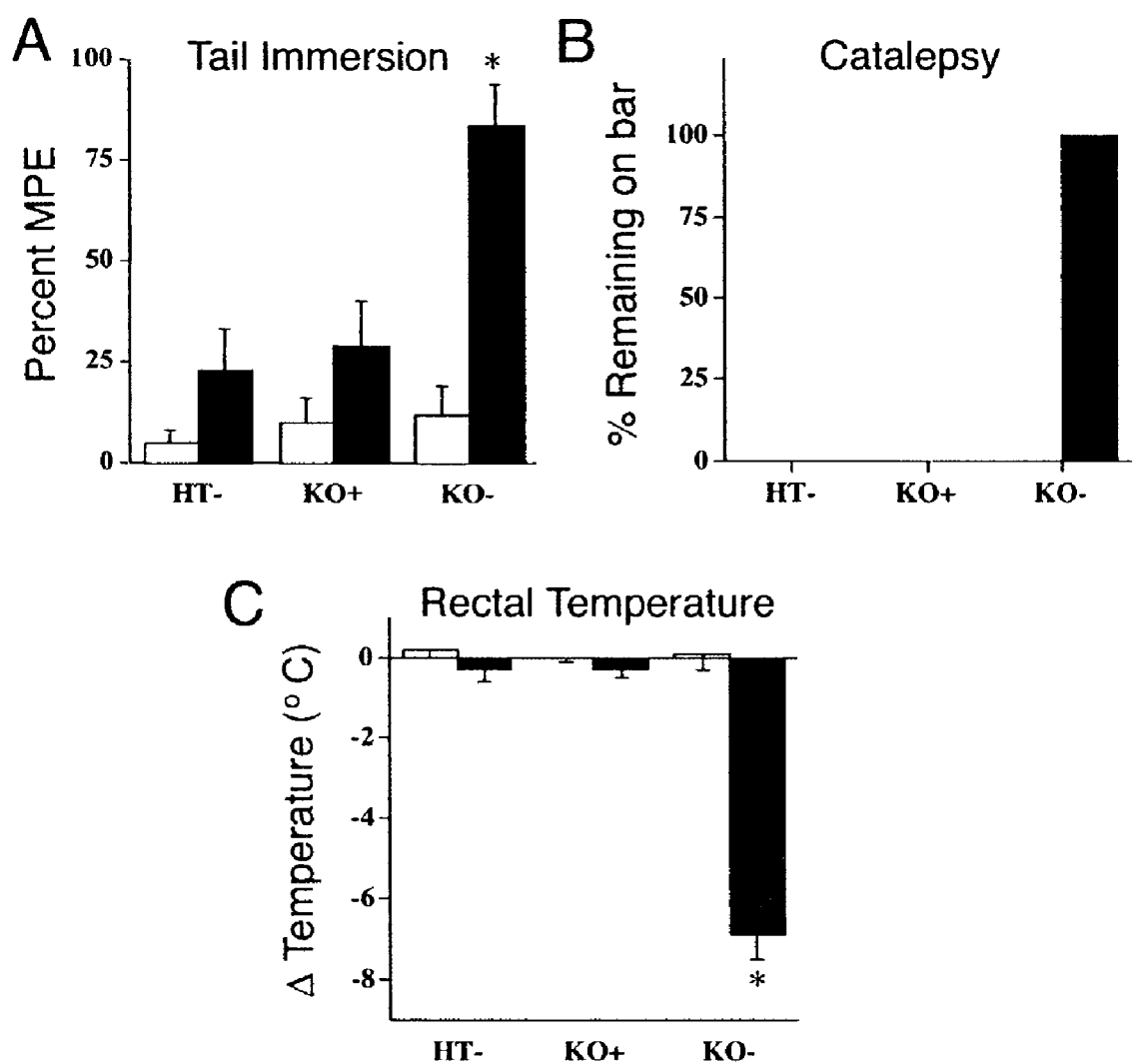

FIG. 6 shows the expression of FAAH specifically in the nervous system (KO+ animals) is sufficient to block the pharmacological effects of anandamide (50 mg/kg, i.p.) on thermal pain sensation (A, tail immersion assay), catalepsy (B, bar test), and rectal temperature (C). *, p<0.01, KO- animals versus either KO+ or HT- animals (planned comparisons); n=6-8 mice per group). Animals were tested at 20 minutes (A) and 60 minute (B and C) following treatment with anandamide. HT-=FAAH(+/-), FAAH-TG(-); KO+=FAAH(-/-), FAAH-TG(+); KO-=FAAH(-/-), FAAH-TG(-).

DETAILED DESCRIPTION OF THE INVENTION

The medicinal properties of marijuana have been recognized for centuries (see, for example, Gurley et al., *J. Psychoactive Drugs* 30:137-147, 1998), but clinical and societal acceptance of this drug as a potential pain therapy remains fiercely debated. An attractive alternative to marijuana-based therapeutics would be to target the molecular pathways that mediate the effects of the drug. The current understanding of these signaling pathways is limited to a receptor ($CB_1$) (see, Pertwee, *Pharmacol. Ther.*, 74:129-180, 1997) that binds the active constituent of marijuana, tetrahydrocannabinol (THC), and an endogenous $CB_1$ ligand anandamide that appears to have weak and transient cannabinoid properties in vivo.

The endogenous cannabinoid system has been the focus of intense research. Cannabinoid receptors have been identified in the brain ($CB_1$ receptor) and in the immune system ($CB_2$ receptor; Pertwee, supra, 1997), and recognize the active component of marijuana, $(-)-\Delta^9$-tetrahydrocannabinol (THC; Mechoulam, in "Cannabinoids as Therapeutic Agents" (CRS Press, Boca Raton, 1986), pages 1 to 19). A natural brain lipid, N-arachidonoyl-ethanolamine ("anandamide") has been characterized as a possible endogenous ligand for the $CB_1$ receptor, but the function of this compound in vivo remains unclear. High doses of anandamide induce only weak and transient cannabinoid behavioral effects in rodents, and efforts to block these responses with the $CB_1$ antagonist SR141716A have met with mixed success. Anandamide produces many of its neurobehavioral effects in $CB_1$ receptor-knockout (CB1$^{-/-}$ mice; DiMarzo et al., *J. Neurochem.* 75:2434-2444, 2000, which is incorporated herein by reference), suggesting that an alternative site of action for this compound exists in vivo. Indeed, anandamide affects multiple receptor systems in addition to the $CB_1$ receptor in vitro, including the capsaicin receptor and gap junctions. As a consequence of these findings, the postulated role of anandamide as an endogenous ligand for the $CB_1$ receptor remains controversial.

The weak cannabinoid properties of anandamide in vivo can result from its expeditious catabolism. Indeed, the half-life of anandamide in vivo is on the order of minutes, severely hindering efforts to characterize the pharmacological and physiological function of this endogenous brain substance. Although numerous proteins and enzymes have been suggested to participate in the rapid catabolism of anandamide, the mechanism by which the level and activity of anandamide are regulated in vivo remain unknown. One candidate enzyme responsible for regulating anandamide function is fatty acid amide hydrolase (FAAH; Cravatt et al., supra, 1996; Giang and Cravatt, supra, 1997), a membrane-bound serine hydrolase that is enriched in brain and liver that hydrolyzes anandamide, and several other bioactive fatty acid amides in vitro, including the postulated $CB_2$ receptor ligand N-palmitoyl ethanolamine and the sleep-inducing lipid oleamide.

Efforts to date to determine the endogenous functions of anandamide have been thwarted by the short half-life of this compound in vivo. In chemical neurotransmission, the amplitude and duration of signals are often tightly regulated by the enzymatic inactivation of the signaling substance. As a consequence, the pharmacological administration of catabolically labile transmitters may fail to report on their physiological functions in vivo. Although several proteins and enzymes have been suggested to participate in the rapid catabolism of anandamide (Cravatt et al., *Nature* 284:83-87, 1996, which is incorporated herein by reference; the results disclosed herein demonstrate that a single degradative enzyme, FAAH (Cravatt et al., supra, 1996), is the key regulator of anandamide signaling in vivo. In FAAH$^{-/-}$ mice, anandamide generated robust $CB_1$ receptor-dependent behavioral effects that rivaled those of THC in terms of efficacy and duration. Additionally, FAAH$^{-/-}$ mice possessed greatly increased endogenous brain levels of anandamide and exhibited thermal analgesia that was reversed by the $CB_1$ antagonist SR141716A. Collectively, these results indicate that anandamide is a potent and selective $CB_1$ ligand in vivo that participates in a FAAH-regulated endogenous cannabinoid tone essential for normal pain transmission. The provocative finding that the amplitude and duration of anandamide's biological activity is primarily regulated by a single enzyme suggests that inhibitors of FAAH may serve as valuable pharmaceutical agents for the treatment of pain and neuropsychiatric disorders.

In order to test the role that FAAH plays in controlling fatty acid amide levels and activity in vivo, a mouse model was generated in which the first exon of the FAAH gene was removed by homologous recombination (see Example 1). As disclosed herein, mice lacking the enzyme fatty acid amide hydrolase (FAAH; see Giang and Cravatt, *Proc. Natl. Acad. Sci., USA* 94:2238-2242, 1997, which is incorporated herein by reference; see, also, Cravatt et al., supra, 1996) are severely impaired in their ability to degrade anandamide and, when treated with this compound, exhibit an array of intense CB1-dependent behavioral responses, including hypomotility, analgesia, catalepsy, and hypothermia (see Example 3). FAAH$^{-/-}$ mice possess endogenous brain levels of anandamide that are fifteen-fold above normal (see Example 2), and display reduced pain sensation that is reversed by the CB1 antagonist SR141716A (see Example 3). These results demonstrate that FAAH is the primary regulator of anandamide signaling in vivo, setting an endogenous cannabinoid tone essential for normal pain transmission. These results further demonstrate that FAAH provides a target for pharmaceutical agents useful for effectively treating pain or neuropsychiatric disorders.

The transgene to be used in the practice of the subject invention is a DNA sequence comprising a modified FAAH sequence. In a preferred embodiment the FAAH gene is disrupted by homologous targeting in embryonic stem cells. For example, the transcriptional and translational start sites of the FAAH gene may be deleted as described in the examples below. Optionally, the FAAH disruption or deletion may be accompanied by insertion of or replacement with other DNA sequences, such as a non-functional FAAH sequence. In other embodiments, the transgene comprises DNA antisense to the coding sequence for FAAH. Where appropriate, DNA sequences that encode proteins having FAAH activity but differ in nucleic acid sequence due to the degeneracy of the genetic code may also be used herein, as may truncated forms, allelic variants and interspecies homologues.

Also included when animals are referred to as transgenic are "knockout animals". For purposes of the subject invention, these animals have been manipulated so that there is disruption or interference with the activity or expression of a gene, i.e., fatty acid amide hydrolase. As used herein, disruption or interference with the activity or expression refers to a manipulation such that the transgenic animal is irreversibly defective for all or essentially all of an activity of one or more specific gene/allele product(s) relative to the corresponding wild type animal. In a particular embodiment of this type, the knockout animal contains within its genome a specific gene/allele that has been inactivated by a method such as gene targeting. As used herein the term "knockout animal" can therefore include the heterozygote animal (e.g., one defective allele and one wild-type allele), a homozygous animal (e.g., two defective alleles) or an animal having more than one gene having at least allele that has been inactivated. In a particular embodiment of the present invention, a knockout animal is a knockout mouse that has both alleles encoding FAAH inactivated. A knockout animal that is heterozygous for a particular gene product activity has been manipulated to be defective for all or "essentially all" of the activity of at least one of the particular allele products relative to the corresponding wild type animal.

As used herein a knockout animal or cell defective for "essentially all" of an activity of a specific gene/allele product, is an animal or cell that has less than about 25% of the gene/allele product activity of the corresponding wild type animal or wild type cell. In a preferred embodiment, the animal or cell has less than or equal to about 20% of the gene/allele product activity of the corresponding wild type animal or wild type cell respectively.

Also provided by the invention is a transgenic mouse comprising a disruption in the fatty acid amide hydrolase (FAAH) gene, wherein the disruption of the FAAH gene results in an inability of the mouse to produce detectable levels of FAAH. FAAH levels can be detected by methods known to those of skill in the art. For example, Western blotting using antibodies that specifically recognize FAAH can be used to assess the relative level of FAAH in tissue samples (see Examples). FAAH antibodies can also be used in immunocytochemical methods to assess the presence of FAAH in tissue sections (see Examples). Such antibodies can also be used in antibody-based assays such as radioimmune assays and enzyme-linked immunoabsorbant assays (ELISA) to determine the level of FAAH.

Also included are transgenes in which the FAAH gene is placed under a promoter to allow specific expression in a subset of tissue or cell types. Such tissue-specific FAAH transgenics animals when crossed with FAAH "knockout" animals would create animals models in which FAAH was only found in a subset of tissues in the body. For example, the inventors have generated such animal models in which FAAH is expressed in the nervous system but not the periphery. This second generation animal model provides a tool for distinguishing central from peripheral pharmacological/physiological activities of FAAH substrates, for example.

A "transgenic" animal can be produced by cross-breeding two chimeric animals which include exogenous genetic material within cells used in reproduction. Twenty-five percent of the resulting offspring will be transgenic i.e., animals that include the exogenous genetic material within all of their cells in both alleles. Fifty percent of the resulting animals will include the exogenous genetic material within one allele and twenty five percent will include no exogenous genetic material.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal.

In another method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191.

In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, 12, Jan. 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention bovine, porcine, ovine and avian animals (e.g., cow, pig, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., *Proc. Natl. Acad. Sci. USA* 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927-6931, 1985; Van der Putten, et al., *Proc. Natl. Acad. Sci USA* 82:6148-6152, 1985). Transfection is easily and efficiently obtained by culturing the blastomeres on a monolayer of virus-producing cells (Van der Putten, supra; Stewart, et al., *EMBO J.* 6:383-388, 1987). Alternatively, infection can be performed at a later stage. Virus or virus-producing cells can be injected into the blastocoele (D. Jahner et al., *Nature* 298:623-628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154-156, 1981; M. O. Bradley et al., *Nature* 309: 255-258, 1984; Gossler, et al., *Proc. Natl. Acad. Sci USA* 83: 9065-9069, 1986; and Robertson et al., *Nature* 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468-1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences that include antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out." An example of a transgene used to "knockout" FAAH function in the present Examples is described in Example 1 or see FIG. 1. Thus, in another embodiment, the invention provides a transgene wherein the first FAAH exon (encoding about amino acids 1 to 65) is deleted.

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous FAAH gene(s), a marker gene fragment can be included in the construct in the 3' untranslated region of the transgene and the Northern probe designed to probe for the marker gene fragment. The levels of FAAH can also be measured in the transgenic animal to establish appropriate expression.

The expression of transgenes can also be assessed by the incorporation of reporter molecules. Reporter molecules, which confer a detectable phenotype on a cell, are well known in the art and include, for example, fluorescent polypeptides such as green fluorescent protein, cyan fluorescent protein, red fluorescent protein, or enhanced forms thereof, an antibiotic resistance polypeptide such as puromycin N-acetyltransferase, hygromycin B phosphotransferase, neomycin (aminoglycoside) phosphotransferase, and the Sh ble gene product; a cell surface protein marker such as the cell surface protein marker neural cell adhesion molecule (N-CAM); an enzyme such as beta-lactamase, chloramphenicol acetyltransferase, adenosine deaminase, aminoglycoside phosphotransferase, dihydrofolate reductase, thymidine kinase, luciferase or xanthine guanine phosphoribosyltransferase polypeptide; or a peptide tag such as a c-myc peptide, a polyhistidine, a FLAG epitope, or any ligand (or cognate receptor), including any peptide epitope (or antibody, or antigen binding fragment thereof, that specifically binds the epitope; see, for example, Hopp et al., *BioTechnology* 6:1204 (1988); U.S. Pat. No. 5,011,912, each of which is incorporated herein by reference). Expression of a reporter molecule can be detected using the appropriate instrumentation or reagent, for example, by detecting fluorescence of a green fluorescent protein or light emission upon addition of luciferin to a luciferase reporter molecule, or by detecting binding of nickel ion to a polypeptide containing a polyhistidine tag. Similarly, expression of a selectable marker such as an antibiotic can be detected by identifying the presence of cells growing under the selective conditions.

A reporter molecule also can provide a means of isolating or selecting a cell expressing the reporter molecule. For example, the reporter molecule can be a polypeptide that is expressed on a cell surface and that contains an operatively linked c-myc epitope; an anti-c-myc epitope antibody can be immobilized on a solid matrix; and cells, some of which express the tagged polypeptide, can be contacted with the matrix under conditions that allow selective binding of the antibody to the epitope. Unbound cells can be removed by washing the matrix, and bound cells, which express the reporter molecule, can be eluted and collected. Methods for detecting such reporter molecules and for isolating the molecules, or cells expressing the molecules, are well known to those in the art (see, for example, Hopp et al., supra, 1988; U.S. Pat. No. 5,011,912). As indicated above, a convenient means of isolating and selecting cells expressing a reporter molecule is provided by using a reporter molecule that confers antibiotic resistance, and isolating cells that grow in the presence of the particular antibiotic.

Also provided by the invention is a method for identifying a compound that specifically inhibits FAAH. The method includes comparing the level of a fatty acid amide following administration of the compound to a non-transgenic mouse to the level of the fatty acid amide in a FAAH transgenic mouse. A similar level of the fatty acid amide in the transgenic mouse and the non-transgenic mouse is indicative of a compound that specifically inhibits FAAH activity.

Fatty acid amides contemplated in the practice of the invention include anandamide, oleamide, palmitoyl ethanolamide, and oleoyl ethanolamide. Oleamide is an endogenous fatty acid primary amide that possesses sleep-inducing properties in animals and has been shown to effect serotonergic systems and block gap junction communication in a structurally specific manner. Palmitoyl ethanolamide is an endogenous fatty acid amide that possess analgesic and anti-inflammatory properties. Oleoyl ethanolamide is an endogenous fatty acid amide that possesses appetite-suppressing activity.

As used herein, "non-transgenic mouse" refers to a wild-type mouse or a mouse in which the activity or expression of the FAAH gene has not been manipulated. In such a non-transgenic mouse, the FAAH level would be expected to be within a normal range. When FAAH is in the normal range, hydrolysis of fatty acid amides takes place quite rapidly resulting in a low level of fatty acid amides in tissue or in plasma. As used herein, the term "wild type," when used in reference to an animal, for example, a wild type mouse, refers to the animal as it exists in nature.

Also provided by the invention is a method for screening a candidate agent for the ability to modulate cannabinoid-mediated behavior in a transgenic animal. The method includes administering to a first transgenic animal a candidate agent and comparing cannabinoid-mediated behavior of the first transgenic animal to the cannabinoid-mediated behavior of a second transgenic animal not administered the candidate agent. A difference in cannabinoid-mediated behavior in the first transgenic animal administered the candidate agent compared to the second transgenic animal not administered the candidate agent is indicative of a candidate agent that modifies cannabinoid-mediated behavior.

A method for identifying a compound that specifically inhibits FAAH activity, which includes comparing the pharmacological activity of anandamide following administration of the candidate FAAH inhibitor to a non transgenic mouse to the pharmacological activity of anandamide in a FAAH transgenic mouse, wherein a similar level of pharmacological activity for anandamide in the transgenic mouse and the non-transgenic mouse is indicative of a compound that specifically inhibits FAAH activity.

Cannabinoid-mediated behavior includes hypomotility, analgesia, hypothermia and catalepsy. Anandamide-mediated behaviors can be assessed by methods know to those of skill in the art and described in Example 3.

The term "candidate agent" is used herein to mean any agent that is being examined for ability to modulate cannabinoid-mediated activity in a method of the invention. Although the method generally is used as a screening assay to identify previously unknown molecules that can act as a therapeutic agent, a method of the invention also can be used to confirm that an agent known to have such activity, in fact has the activity, for example, in standardizing the activity of the therapeutic agent.

A candidate agent can be any type of molecule, including, for example, a peptide, a peptidomimetic, a polynucleotide, or a small organic molecule, that one wishes to examine for the ability to act as a therapeutic agent, which is an agent that provides a therapeutic advantage to a subject receiving it. It will be recognized that a method of the invention is readily adaptable to a high throughput format and, therefore, the method is convenient for screening a plurality of test agents either serially or in parallel. The plurality of test agents can be, for example, a library of test agents produced by a combinatorial method library of test agents. Methods for preparing a combinatorial library of molecules that can be tested for therapeutic activity are well known in the art and include, for example, methods of making a phage display library of peptides, which can be constrained peptides (see, for example, U.S. Pat. Nos. 5,622,699; 5,206,347; Scott and Smith, Science 249:386-390, 1992; Markland et al., Gene 109:1319, 1991; each of which is incorporated herein by reference); a peptide library (U.S. Pat. No. 5,264,563, which is incorporated herein by reference); a peptidomimetic library (Blondelle et al., Trends Anal. Chem. 14:8392, 1995; a nucleic acid library (O'Connell et al., supra, 1996; Tuerk and Gold, supra, 1990; Gold et al., supra, 1995; each of which is incorporated herein by reference); an oligosaccharide library (York et al., Carb. Res., 285:99128, 1996; Liang et al., Science, 274:1520-1522, 1996; Ding et al., Adv. Expt. Med. Biol., 376:261-269, 1995; each of which is incorporated herein by reference); a lipoprotein library (de Kruif et al., FEBS Lett., 399:232-236, 1996, which is incorporated herein by reference); a glycoprotein or glycolipid library (Karaoglu et al., J. Cell Biol., 130:567-577, 1995, which is incorporated herein by reference); or a chemical library containing, for example, drugs or other pharmaceutical agents (Gordon et al., J. Med. Chem., 37:1385-1401, 1994; Ecker and Crooke, Bio/Technology, 13:351-360, 1995; each of which is incorporated herein by reference). Accordingly, the present invention also provides a therapeutic agent identified by such a method, for example, a neuroactive therapeutic agent.

The route of administration of a candidate agent will depend, in part, on the chemical structure of the candidate agent. Peptides and polynucleotides, for example, are not particularly useful when administered orally because they can be degraded in the digestive tract. However, methods for chemically modifying peptides, for example, to render them less susceptible to degradation by endogenous proteases or more absorbable through the alimentary tract are well known (see, for example, Blondelle et al., Trends Anal. Chem. 14:83-92, 1995; Ecker and Crooke, Bio/Technology, 13:351-360, 1995; each of which is incorporated herein by reference). In addition, a peptide agent can be prepared using D-amino acids, or can contain one or more domains based on peptidomimetics, which are organic molecules that mimic the structure of peptide domain; or based on a peptoid such as a vinylogous peptoid.

A candidate agent can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the candidate agent can be administered by injection, intubation, orally or topically, the latter of which can be passive, for example, by direct application of an ointment, or active, for example, using a nasal spray or inhalant, in which case one component of the composition is an appropriate propellant.

The total amount of a candidate agent to be administered in practicing a method of the invention can be administered to a subject as a single dose, either as a bolus or by infusion over a relatively short period of time, or can be administered using a fractionated treatment protocol, in which multiple doses are administered over a prolonged period of time. The candidate agent can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

Also provided by the invention is a method for screening a candidate agent for the ability to modulate behavior in a FAAH transgenic animal. Such candidate agents include a FAAH substrate, or a compound that alters the levels or activities of endogenous FAAH substrates (e.g. cannabinoid receptor antagonist). The method includes administering to a first transgenic animal a candidate agent and comparing the behavior of the first transgenic animal to the behavios of a second transgenic animal not administered the candidate agent or a non-transgenic animal administered the candidate agent. A difference in behavior in the first transgenic animal administered the candidate agent compared to the second transgenic animal not administered the candidate agent or the non-transgenic animal administered the candidate agent is indicative of a candidate agent that modifies behavior in FAAH-dependent way.

The following examples are intended to illustrate but not limit the invention.

EXAMPLE 1

Generation of FAAH Knockout Mice

This example provides a method for generating fatty acid amide hydrolase (FAAH) knockout mouse using homologous recombination to disrupt the endogenous FAAH gene.

Figure 1:
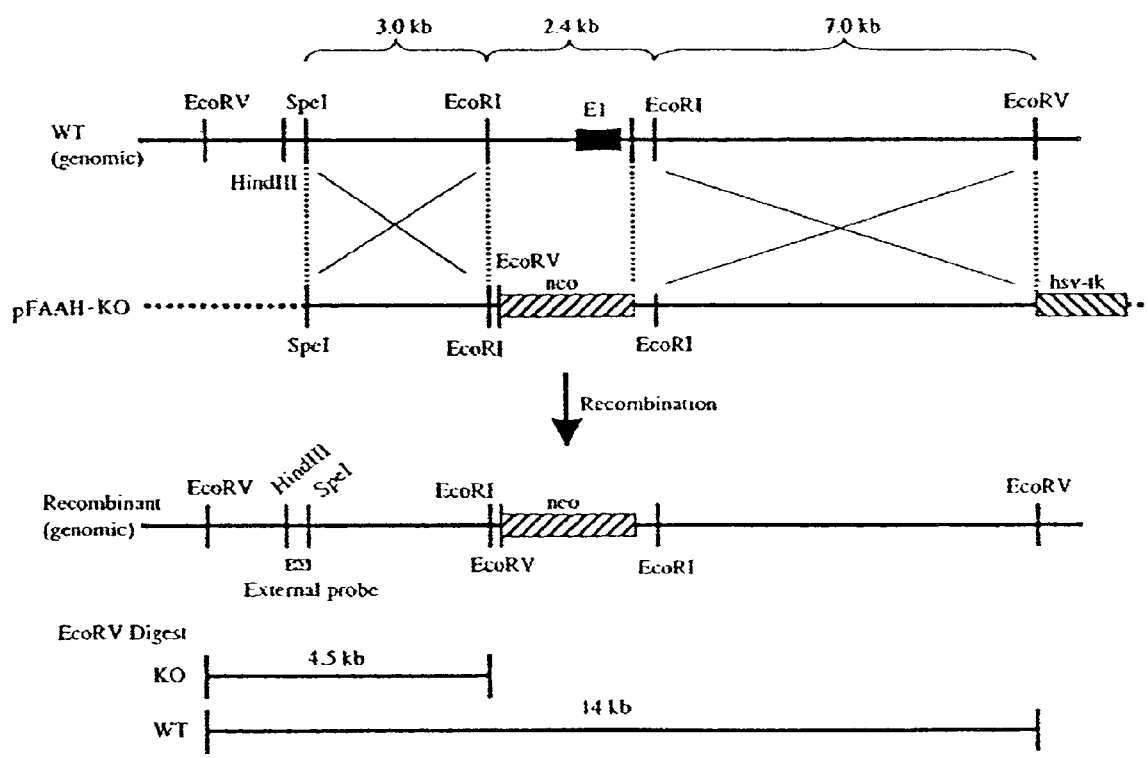
FIGS. 1 illustrates the generation and biochemical characterization of FAAH$^{-/-}$ mice.

The FAAH gene was isolated from a 129SvJ genomic library and a 2.5 kb region encompassing the first exon was mapped and sequenced (see FIG. 1). A targeting vector, pFAAH-KO was constructed by inserting the PGK-Neo cassette between the Eco RI and Eco RV sites located 2.3 kb apart in the FAAH gene, replacing the first FAAH exon (encoding amino acids 1 to 65) and approximately 2 kb of upstream sequence (see FIG. 1).

Homologous recombination in 129SvJ embryonic stem cell clones was identified by Southern blot analysis using the probe shown in FIG. 1. For Southern blot analysis, genomic DNA was isolated from the transfected stem cell clones, digested with EcoRV, then separated by electrophoresis, transferred to nylon filters, and hybridized with the labeled probe. Two clones showing the 4.5 kb band expected due to homologous recombination (see FIG. 1) were isolated and used to generate chimeric mice on a C57BL/6 background.

Chimeras from both clones demonstrated germline transmission of the mutated gene. $FAAH^{-/-}$ mice were born at the expected Mendelian frequency and were viable, fertile, and largely indistinguishable from wild type littermates. Offspring from both clones were tested and provided indistinguishable results. No differences were observed in general appearance, body weight, locomotion, or overt behavior. Second or third generation offspring from intercrosses of 129SvJ-C57BL/6 $FAAH^{+/-}$ mice were used in the experiments described below.

EXAMPLE 2

Biochemical Characterization of FAAH Knockout Mice

This example provides biochemical assays useful for characterizing the FAAH knockout mice.

Brain and liver were isolated from homozygous wild type ($FAAH^{+/+}$), heterozygous ($FAAH^{+/-}$) and homozygous knockout ($FAAH^{-/-}$) mice and examined by western blot analysis using polyclonal anti-FAAH antibodies (see Patricelli et al., Biochemistry 37:15177-15187, 1998). No FAAH protein was detectable in the brain or liver of the knockout mice.

The mice also were examined for FAAH enzymatic activity. FAAH activity assays for oleamide and anandamide were measured by following the conversion of $^{14}C$-labeled substrates using a thin layer chromatography assay essentially as described by Patricelli et al. (Biochemistry 38:9804-9812, 1999), except that enzyme assays were conducted at pH 7.2. Brain and liver from $FAAH^{-/-}$ mice exhibited greatly reduced FAAH catalytic activity (Table 1). Brain extracts from $FAAH^{-/-}$ mice hydrolyzed anandamide and oleamide 50 to 100 times more slowly than brain extracts from the homozygous wild type mice.

EXAMPLE 3

Neurobehavioral Examination of FAAH Knockout Mice

This example provides neurobehavioral assays that measure spontaneous activity, thermal pain sensation, catalepsy, and rectal temperature, and demonstrates that FAAH regulates anandamide activity in vivo.

Experiments were performed using a combination of male and female mice (no significant sex differences were observed for either genotype). All drugs were administered intraperitoneal (ip) in a mixture of 1 part ethanol: 1 part EMULPHOR alcohol (GAF Corp.; New York N.Y.): 18 parts saline (10 μl/g body weight), except naloxone was administered ip in saline.

Locomotor activity was assessed by placing each mouse in a clear plexiglass cage (18×10×8.5 inches; l.w.h) that was marked in 7 cm square grids on the floor of the cage. The number of grids that were traversed by the hind paws was counted from 15 to 20 min post-injection. Nociception was assessed using the tail immersion assay, wherein each mouse was hand-held with approximately 1 cm of the tip of the tail immersed into a water bath maintained at 56.0° C. and the latency for the animal to withdraw its tail was scored. The cutoff was 15 sec, and the data were expressed as the percent maximum possible effect (% MPE), where % MPE=100×{(post-injection latency−pre-injection latency)/(15−pre-injection latency)}. Baseline thermal nociception was also analyzed using the hot plate test, wherein the latency to jump or lick/shake a hind paw was scored.

Catalepsy was evaluated using the bar test, in which the front paws of each subject were placed on a rod (0.75 cm diameter) that was elevated 4.5 cm above the surface. Mice that remained motionless with their paws on the bar for 10 sec (with the exception of respiratory movements) were scored as cataleptic. Rectal temperature was determined by inserting a thermocouple probe 1.2 cm into the rectum; the temperature was obtained using a telethermometer. The pre-injection rectal temperatures for $FAAH^{+/+}$ (35.6±0.2° C., n=28) and $FAAH^{-/-}$ mice (35.5±0.1° C., n=30) mice were equivalent. Catalepsy and rectal temperature were assessed at 60 min post-injection unless otherwise indicated.

Figure 2:
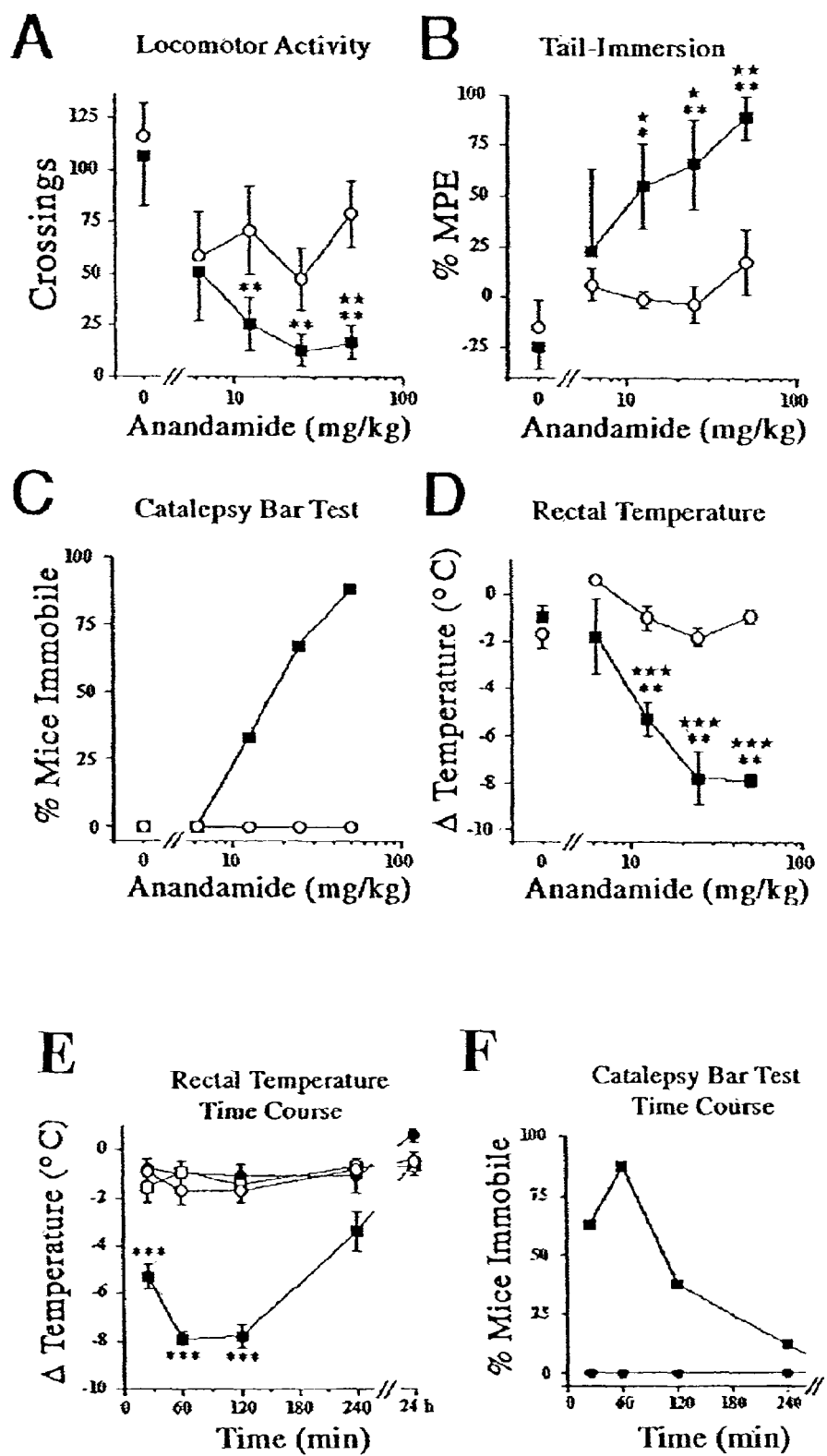
FIGS. 2A to 2F show the pharmacological activity of anandamide in FAAH$^{+/+}$ (open circles) and FAAH$^{-/-}$ mice filled squares).
Figure 3:
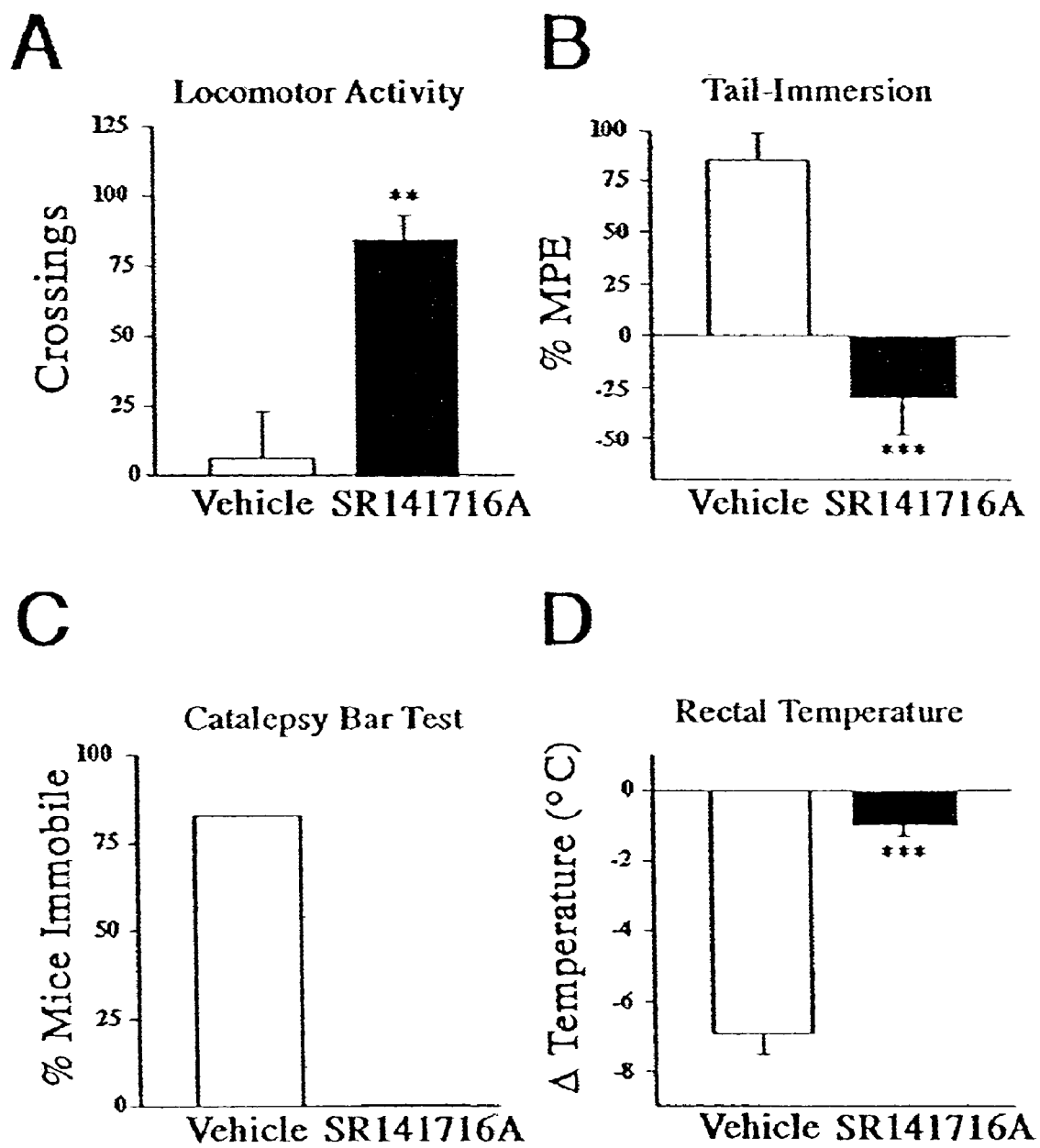
FIGS. 3A to 3D demonstrate that the behavioral effects due to anandamide in FAAH$^{-/-}$ mice are mediated by the CB1 cannabinoid receptor. The effect of vehicle (open columns) or SR141716A (filled columns) administered 10 min prior to treatment with anandamide in FAAH$^{-/-}$ mice.

Anandamide failed to produce any significant effects in $FAAH^{+/+}$ mice over the dose range examined (6.25 to 50 mg/kg; see FIGS. 2A to 2D). In contrast, anandamide produced a robust, dose-dependent pharmacological activity in $FAAH^{-/-}$ mice, causing hypomotility (FIG. 2A), analgesia (FIG. 2B), catalepsy (FIG. 2C), and hypothermia (FIG. 2D). At the highest dose tested (50 mg/kg) in the $FAAH^{-/-}$ mice, anandamide induced an 84±8% reduction in spontaneous activity, dramatic analgesia in the tail immersion test (89±11% maximum possible effect, "MPE"), strong cataleptic behavior in the bar test (88% of the test group), and a 7.9±0.3° C. reduction in rectal temperature (see FIG. 2).

The striking impact of anandamide on the behavior of $FAAH^{-/-}$ mice was readily detected within five min of treatment, at which time the animals adopted a flattened, rigid posture and remained completely motionless with their eyes open. If startled by sound or touch, the knockout mice reacted with brief fits of spastic movement, then quickly reentered a flattened, immobile state. Anandamide-treated $FAAH^{-/-}$ mice remained immobile for 2 to 4 hr, depending on dose, after which they gradually reinitiated normal cage activities, including movement, rearing, and grooming.

The duration of the behavioral effects due to anandamide in $FAAH^{-/-}$ mice also was examined by measuring rectal temperature and catalepsy at various times post-treatment. Coinciding closely with their overt cage behavior, the anandamide-treated $FAAH^{-/-}$ mice (50 mg/kg) showed a robust drop in rectal temperature that peaked between 1 and 2 hr after treatment and began to return to wild type values by 4 hr (FIG. 2E). Similarly, catalepsy was most extreme at 1 hr post-treatment and gradually dissipated by 4 hr (FIG. 2F). $FAAH^{-/-}$ mice were indistinguishable from $FAAH^{+/+}$ mice when analyzed 24 hr after treatment with anandamide.

The intense behavioral effects induced by anandamide in $FAAH^{-/-}$ mice were reminiscent of those traditionally observed in rodents treated with THC (Smith et al., supra, 1994), suggesting that anandamide acts as an endogenous CB1 ligand. To determine the contribution of CB1 receptor pathways to the behavioral pharmacology elicited by anandamide in $FAAH^{-/-}$ mice, the CB1 antagonist SR141716A (10 mg/kg, ip) was administered 10 min prior to treatment with anandamide (50 mg/kg). Remarkably, all of the behavioral effects of anandamide in the $FAAH^{-/-}$ mice were completely blocked by pretreatment with SR141716A (FIGS. 3A to 3D). In contrast, pretreatment with the opioid receptor antagonist naloxone (2 mg/kg, ip) failed to reduce any activity due to anandamide in the $FAAH^{-/-}$ mice.

The profound CB1-dependent pharmacological effects induced by anandamide in $FAAH^{-/-}$ mice initially suggested that a sensitized or upregulated CB1 receptor system exists in these animals. However, $FAAH^{-/-}$ and $FAAH^{+/+}$ mice exhibited nearly identical THC dose response profiles for all of the behavioral assays tested (Table 2), indicating that their CB1 receptors were functionally equivalent. Collectively, these results indicate that, in the absence of FAAH, anandamide acts as an exceptionally potent and selective CB1 agonist in vivo.

During the course of characterizing the pharmacological effects of anandamide in $FAAH^{+/+}$ and $FAAH^{-/-}$ mice, baseline measures of spontaneous activity, rectal temperature, and pain sensitivity were recorded. $FAAH^{-/-}$ mice did not differ from $FAAH^{+/+}$ mice in terms of their respective locomotor activities or rectal temperatures (FIGS. 2A and 2D). However, $FAAH^{-/-}$ mice displayed altered thermal pain sensation, exhibiting prolonged response latencies in both the tail immersion and hot plate tests (FIG. 4A). In the hot plate test, $FAAH^{-/-}$ mice differed significantly from $FAAH^{+/+}$ mice over a restricted temperature range (FIG. 4A, right panel). Interestingly, a similar phenotype was observed in the substance P/neurokinin A knockout mouse and interpreted to implicate these peptides in neural pathways that communicate moderate to intense pain stimuli (Cao et al., Nature 392:390-394, 1996).

The reduced pain perception exhibited by $FAAH^{-/-}$ mice suggested that these animals possessed enhanced levels of endogenous cannabinoid activity. To explore this notion further, brain levels of anandamide and related N-acylethanolamines (NAEs) were measured by isotope dilution liquid chromatography mass spectrometry (LC-MS; DiMarzo et al., supra, 2000). Mice were anesthetized using $CO_2/O_2$ and sacrificed by decapitation. Brains were removed and immediately homogenized in a 2:1:1 mixture of chloroform:methanol:50 mM Tris (pH 8.0) containing N-oleoyl-$d_4$-ethanolamine and $d_4$-anandamide standards (0.5 nmol each per brain). The organic layer was removed, dried under nitrogen gas, and washed with ethyl acetate, then the washes were transferred to a fresh glass vial and dried. The remaining residue was solubilized in methanol and injected onto an Agilent 1100 series LC-MS. Levels of endogenous NAEs were quantified by comparing their mass ion peak heights to those of the corresponding isotopically labeled standards. Standard curves were generated to confirm a linear relationship between peak height and NAE concentration.

Strikingly, brains from $FAAH^{-/-}$ mice possessed 15-fold higher levels of anandamide than brains from $FAAH^{+/+}$ mice (FIG. 5A). Endogenous brain levels of N-oleoyl ethanolamine were 710+90 and 18+12 pmol/g tissue for $FAAH^{-/-}$ and $FAAH^{+/+}$ mice, respectively. Although a standard for N-palmitoyl ethanolamine was not included in the assay, a peak corresponding to the molecular mass of this lipid (m/z=300.3) was greatly increased in $FAAH^{-/-}$ samples (relative to the included NAE standards), indicating that brain levels of this NAE were also upregulated in these animals. Other NAEs, including N-oleoyl ethanolamine and N-palmitoyl ethanolamine, were similarly upregulated, consistent with shared biosynthetic and degradative pathways for these lipids.

To test whether enhanced levels of endogenous anandamide were responsible for the analgesia observed in $FAAH^{-/-}$ mice, the pain responses of these animals and $FAAH^{+/+}$ mice were tested prior to and after treatment with vehicle or with SR141716A. Vehicle-treated $FAAH^{+/+}$ mice and $FAAH^{-/-}$ mice and SR141617A-treated $FAAH^{+/+}$ mice all displayed modest increases in their hot plate response latencies that failed to reach significance (FIG. 5B). In sharp contrast to these three test groups, $FAAH^{-/-}$ mice treated with SR141716A showed a dramatic reduction in their response latencies (FIG. 5Cl), indicating that a substantial fraction of their thermal pain sensation was mediated by CB1 receptor pathways.

These results demonstrate that mice lacking FAAH are severely impaired in their ability to degrade anandamide and, when treated with this compound, exhibit an array of intense CB-1-dependent behavioral responses. The results further demonstrate that FAAH is the primary regulator of anandamide signaling in vivo, setting an endogenous cannabinoid tone essential for normal pain transmission.

EXAMPLE 4

Generation of a Mouse Model with FAAH Expression Restricted to the Nervous System Exogenously applied and endogenously produced fatty acid amides induce a variety of behavioral effects in mammals, which may reflect either central or peripheral sites of action. In wild type mammals, FAAH is not only expressed in the central and peripheral nervous system, but also in a variety of non-nervous system peripheral tissues, including liver, kidney, and testis. Thus, a standard deletion of the FAAH gene results in an animal model where FAAH is absent from all sites in the organism and therefore does not permit an assignment of phenotypes to central or peripheral modes of action. To address this issue, the mouse FAAH cDNA was placed under the control of the neural specific enolase (NSE) promoter (Forss-Petter et al. (1990) Neuron 5, 187-197) and this construct was used to generate transgenic mice (mixed background of C57Bl/6 and Balb/c) by pronuclear injection methods following standard literature procedures (Gordon, J. W. (1993) Methods Enzymol. 225, 747-771). These animals were screened by Southern blotting for genomic incorporation of the FAAH gene and multiple FAAH-positive transgenic [FAAH-TG(+)] lines were identified. One of these FAAH-TG(+) lines was then crossed to mice heterozygotic for FAAH deletion [FAAH(+/−) mice]. To create representative mouse genotypes for biochemical and behavioral analysis, the following breeding pairs were set up: FAAH(+/−),FAAH-TG(+)×FAAH(−/−),FAAH-TG(−). The following genotypes from these breeding pairs were comparatively characterized: FAAH(+/−), FAAH-TG(−) mice, FAAH(−/−), FAAH-TG(+) mice, and FAAH (−/−), FAAH-TG(−) mice.

FAAH(−/−), FAAH-TG(+) mice express FAAH in the nervous system, but not the periphery. Western blot analysis using anti-FAAH polyclonal antibodies demonstrated that FAAH expression in FAAH(−/−), FAAH-TG(+) mice was restricted to the central and peripheral nervous system. No detectable FAAH protein was observed in the liver, testis, kidney, or heart of these animals.

The behavioral effects of anandamide are dramatically reduced in FAAH(−/−), FAAH-TG(+) mice. A comparative characterization of the pharmacological effects of anandamide in FAAH(+/−), FAAH-TG(−) mice, FAAH(−/−), FAAH-TG(+) mice, and FAAH(−/−), FAAH-TG(−) mice revealed that only the last group of animals displayed significant behavioral effects to this endocannabinoid (FIG. 6). These data reveal that the expression of FAAH in the nervous system is sufficient to block anandamide-induced thermal analgesia, catalepsy, and hypothermia.

Although the invention has been described with reference to the above examples, it will be understood that modifications and variations are encompassed within the spirit and scope of the invention. Accordingly, the invention is limited only by the following claims.

What is claimed is:

1. A method for screening a candidate agent for an ability to modulate a cannabinoid-mediated behavior in a transgenic mouse comprising:
    (a) administering to a first transgenic mouse the candidate agent, and
    (b) comparing the cannabinoid-mediated behavior of the first transgenic mouse to the cannabinoid-mediated behavior of a second transgenic mouse not administered the candidate agent;
    wherein a difference in the cannabinoid-mediated behavior in the first transgenic mouse administered the candidate agent compared to the second transgenic mouse not administered the candidate agent indicates that the candidate agent modifies the cannabinoid-mediated behavior; and
    wherein the transgenic mouse has a homozygous transgene which (i) disrupts or interferes with expression of an endogenous fatty acid amide hydrolase (FAAH) gene, and (ii) is chromosomally integrated into germ cells of the mouse.

2. The method of claim 1, wherein the cannabinoid-mediated behavior is hypomotility.

3. The method of claim 1, wherein the cannabinoid-mediated behavior is analgesia.

4. The method of claim 1, wherein the cannabinoid-mediated behavior is hypothermia.

5. The method of claim 1, wherein the cannabinoid-mediated behavior is catalepsy.

6. A method for screening a candidate agent for an ability to modulate a behavior in a transgenic mouse comprising:
    (a) administering to a first transgenic mouse of the candidate agent, and
    (b) comparing the behavior of the first transgenic mouse to the behavior of a second transgenic mouse not administered the candidate agent or a non-transgenic mouse administered the candidate agent;
    wherein a difference in behavior in the first transgenic mouse administered the candidate agent compared to the second transgenic mouse not administered the candidate agent or the non-transgenic mouse administered the candidate agent indicates that the candidate agent modifies the behavior in an FAAH-dependent way; and
    wherein the transgenic mouse has a homozygous transgene which (i) disrupts or interferes with expression of an endogenous fatty acid amide hydrolase (FAAH) gene, and (ii) is chromosomally integrated into germ cells of the mouse.

7. The method of claim 6, wherein the behavior is pain sensation, sleep, learning, memory, fear, schizophrenia, motility, thermoregulation, epilepsy, neurodegeneration, feeding, alcohol consumption, or drug consumption/metabolism.

* * * * *